United States Patent
Addiego et al.

(10) Patent No.: US 11,351,302 B2
(45) Date of Patent: Jun. 7, 2022

(54) MONITORING UPSTREAM FLOW CHARACTERISTICS FOR A PUMP

(71) Applicant: CareFusion 303, Inc., San Diego, CA (US)

(72) Inventors: Nicholas Addiego, San Diego, CA (US); Shannon Bailey, San Diego, CA (US); Robert Dwaine Butterfield, San Diego, CA (US); Denton Davis, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 73 days.

(21) Appl. No.: 16/601,225

(22) Filed: Oct. 14, 2019

(65) Prior Publication Data

US 2020/0114072 A1 Apr. 16, 2020

Related U.S. Application Data

(60) Provisional application No. 62/745,910, filed on Oct. 15, 2018.

(51) Int. Cl.
*A61M 5/168* (2006.01)

(52) U.S. Cl.
CPC ........ *A61M 5/1684* (2013.01); *A61M 5/1689* (2013.01); *A61M 5/16881* (2013.01); *A61M 2205/18* (2013.01); *A61M 2205/3351* (2013.01); *A61M 2205/3389* (2013.01); *A61M 2205/581* (2013.01); *A61M 2205/583* (2013.01)

(58) Field of Classification Search
CPC ......... A61M 2005/16872; A61M 2005/16863; A61M 5/1684; A61M 5/1689; A61M 2205/3351; A61M 2205/3389; A61M 5/16877; A61M 5/16881; A61M 5/1411; A61M 2205/18; A61M 2205/581; A61M 2205/583

See application file for complete search history.

(56) References Cited

U.S. PATENT DOCUMENTS

| | | | | |
|---|---|---|---|---|
| 4,105,028 A | * | 8/1978 | Sadlier | A61M 5/1689 128/DIG. 13 |
| 4,718,896 A | * | 1/1988 | Arndt | A61M 5/1689 604/253 |
| 5,096,385 A | * | 3/1992 | Georgi | A61M 5/16859 417/18 |
| 5,356,378 A | * | 10/1994 | Doan | A61M 5/16859 128/DIG. 13 |

(Continued)

FOREIGN PATENT DOCUMENTS

EP  3421064 A1  1/2019

*Primary Examiner* — Nilay J Shah
(74) *Attorney, Agent, or Firm* — Mintz, Levin, Cohn, Ferris, Glovsky and Popeo, P.C.

(57) ABSTRACT

A system for monitoring upstream flow characteristics for a pump is provided. The system may receive one or more outputs from a fluid level sensor coupled with a pump. The system may detect based on at least the one or more outputs, an abnormal upstream flow condition in the pump, such as a full upstream occlusion in the tube, a partial upstream occlusion in the tube, an empty reservoir, and/or a backflow of the fluid into the drip chamber. The system may adjust, based on the detection of an abnormal upstream flow condition in the pump, operation of the pump.

20 Claims, 7 Drawing Sheets

(56) References Cited

U.S. PATENT DOCUMENTS

| | | | | |
|---|---|---|---|---|
| 5,827,223 | A | * | 10/1998 | Butterfield ........ A61M 5/16859 604/65 |
| 10,226,571 | B2 | | 3/2019 | Davis et al. |
| 2005/0145009 | A1 | * | 7/2005 | Vanderveen ........ A61M 5/1684 73/1.57 |
| 2012/0095433 | A1 | * | 4/2012 | Hungerford ........ A61M 5/1684 604/500 |
| 2013/0177455 | A1 | * | 7/2013 | Kamen .................. F04B 43/12 417/313 |
| 2016/0206809 | A1 | * | 7/2016 | Kamen ............ A61B 5/150358 |
| 2017/0290974 | A1 | | 10/2017 | Tsoukalis |
| 2018/0099089 | A1 | | 4/2018 | Vanderveen et al. |

* cited by examiner

MONITORING UPSTREAM FLOW CHARACTERISTICS FOR A PUMP

CROSS-REFERENCE TO RELATED APPLICATIONS

This application claims priority to U.S. Provisional Patent Application No. 62/745,910, entitled "MONITORING UPSTREAM FLOW CHARACTERISTICS FOR A PUMP" and filed on Oct. 15, 2018, the entirety of which is incorporated herein by reference in its entirety.

TECHNICAL FIELD

The subject matter disclosed herein relates generally to fluid dynamics and more specifically to techniques for monitoring the upstream flow characteristics of a peristaltic pump.

BACKGROUND

A pump may be used for moving fluids, for example, from a reservoir to a desired destination. For example, a peristaltic pump may be a type of positive displacement pump used for delivering intravenous fluids including, for example, volume expanders, blood-based products, blood substitutes, medications, nutrition, and/or the like. The peristaltic pump may operate by applying continuous pressure to a flexible tube containing an intravenous fluid. For instance, the peristaltic pump may include a rotor having one or more rollers, wipers, and/or lobes disposed along its external circumference. As the rotor rotates, the rollers, wipers, and/or lobes may compress successive portions of the flexible tube, thereby forcing the intravenous fluid through the flexible tube and into, for example, a drip chamber.

SUMMARY

In some example embodiments, there are provided systems and methods for monitoring the upstream flow characteristics of a pump. For example, the pump may be coupled with multiple sensors including, for example, a drop sensor, a pressure sensor, and a fluid level sensor. The outputs from the drop sensor, the pressure sensor, and the fluid level sensor may be used to detect various abnormalities in the upstream flow characteristics of the pump including, for example, a full upstream occlusion, a partial upstream occlusion, an empty reservoir, a backflow, and/or the like.

According to some implementations, a system may receive, from a fluid level sensor, one or more outputs. The fluid level sensor may be coupled with a pump. The pump may move a fluid from a reservoir containing the fluid to a drip chamber. The fluid may be moved through a tube upstream from the pump. The system may also detect, based at least on the one or more outputs, an abnormal upstream flow condition in the pump. The abnormal upstream flow condition may include a full upstream occlusion in the tube, a partial upstream occlusion in the tube, an empty reservoir, and/or a backflow of the fluid into the drip chamber. The system may adjust, based on the detection of an abnormal upstream flow condition in the pump, operation of the pump.

In some implementations, the fluid level sensor may measure a fluid level in the drip chamber by at least transmitting a signal and measuring a quantity of time required for the signal to travel through the fluid in the drip chamber. In some implementations, the fluid level sensor is configured to detect drops of the fluid entering the drip chamber by at least measuring the fluid level in the drip chamber at a greater frequency than a frequency at which the drops of the fluid enter the drip chamber. In some implementations, the fluid level sensor detects the drops of the fluid entering the drip chamber instead of a drop sensor.

In some implementations, the full upstream occlusion in the tube is detected when a fluid level in the drip chamber remains fixed.

In some implementations, the partial upstream occlusion in the tube is detected, when a fluid level in the drip chamber decreases while drops of the fluid continue to enter the drip chamber. In some implementations, the partial upstream occlusion in the tube is detected, when drops of the fluid continue to enter the drip chamber at a drip rate that is less than an expected drip rate for the pump. In some implementations, the system predicts that the empty reservoir, the full upstream occlusion in the tube, and/or the partial upstream occlusion in the tube will occur, when a fluid level in the drip chamber decreases while no drops of fluid enter the drip chamber. In some implementations, the backflow of the fluid into the drip chamber is detected based at least on an increase in a fluid level in the drip chamber.

In some implementations, the system may receive, from a drop sensor and a pressure sensor, one or more outputs. The drop sensor and the pressure sensor may be coupled with the pump. The system may detect based at least on the one or more outputs of the drop sensor, the pressure sensor, and the fluid level sensor, the abnormal upstream flow condition in the pump.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to the upstream flow characteristics of a pump, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the subject matter disclosed herein. In the drawings.

When practical, similar reference numbers denote similar structures, features, or elements.

DETAILED DESCRIPTION

A pump may encounter a variety of abnormal upstream flow conditions during its operation including, for example, a full upstream occlusion, a partial upstream occlusion, an empty reservoir, a backflow, and/or the like. Conventional techniques for monitoring the upstream flow characteristics of a pump may be incapable of detecting some abnormal upstream flow conditions. For example, a pump may continue to output drops of fluid, despite the presence of a backflow and/or a partial upstream occlusion. The decrease in the drip rate and/or the size of the drops caused by the backflow and/or partial upstream occlusion may be gradual and therefore imperceptible to conventional monitoring techniques. As such, in some example embodiments, a pump may be coupled with a plurality of sensors including, for example, a pressure sensor, a drop sensor, and a fluid level sensor. The outputs from the drop sensor, the pressure sensor, and the fluid level sensor may enable the detection of a variety of abnormalities in the upstream flow characteristics of the pump including, for example, a full upstream occlusion, a partial upstream occlusion, an empty reservoir, a backflow, and/or the like.

Figure 1:
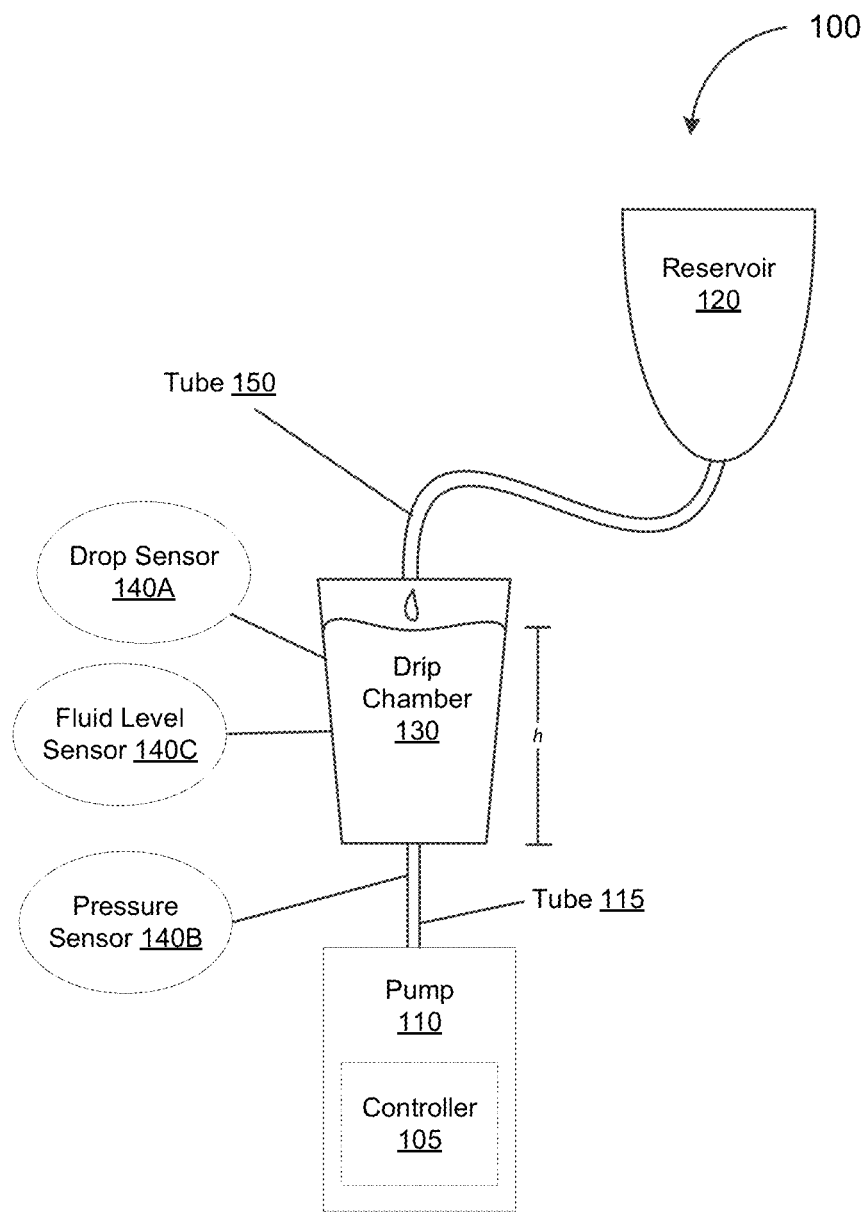
FIG. 1 depicts a block diagram illustrating a pump system, in accordance with some example embodiments.

FIG. 1 depicts a block diagram illustrating a pump system 100, in accordance with some example embodiments. The pump system 100 may include a pump 110, which may be any type of pump configured to move a fluid from a drip chamber 130 to a destination (not shown) such as, for example, a patient. For instance, in some example embodiments, the pump 110 may be a peristaltic pump. As shown in FIG. 1, in order move the fluid from the drip chamber 130, the pump 110 may move the fluid through a tube 115 upstream from the pump 110. The pump 110 may further move the fluid through a tube 150 downstream from the pump 110 and leading to the destination (not shown).

In some example embodiments, the pump 110 may be coupled with multiple sensors including, for example, a drop sensor 140A, a pressure sensor 140B, and a fluid level sensor 140C. The sensors may each record measurements at the same or varying rates. In other words, the sensors may each record measurements periodically at various frequencies.

The drop sensor 140A may detect and/or record one or more parameters of the fluid, such as a drip rate (e.g., a rate at which drops of the fluid flow into the drip chamber 130). The pump system 110 (e.g., via a controller 105) may compare the drip rate to a threshold drip rate and/or determine whether any deviation in drip rate from a threshold or predetermined drip rate is within a tolerance. In some implementations, the tolerance is 10% (e.g., at least 10% deviation in recorded drip rate from an expected drip rate). Thus, an abnormal upstream flow condition in the pump may be detected when the recorded drip rate is at least 10% higher and/or lower than the expected drip rate. In some implementations, the threshold and/or tolerance is an approximately 1% to 5%, 5% to 10%, 10% to 20% or greater deviation in the recorded drip rate from an expected drip rate (e.g., an expected drip rate, pressure, vacuum, fluid level, and the like). The expected drip rate may depend on a number of factors, such as a patient set, order, or prescription, and/or a size of one or more components of the pump system, such as the drip chamber 130. In some implementations, the expected drip rate is approximately 5 drops per minute. In other implementations, the expected drip rate is approximately 1 to 5 drops per minute, 5 to 10 drops per minute, 10 to 15 drops per minute, 15 to 20 drops per minute, 20 to 25 drops per minute, 25 to 30 drops per minute or more.

For example, based on the one or more parameters, the drop sensor 140A may detect whether drops of fluid are flowing into the drip chamber 130, whether the drops of fluid are flowing into the drip chamber 130 at a drip rate that is too high (e.g., the drops of fluid are flowing into the drip chamber 130 too quickly, such as when the recorded drip rate is at least 10% (or the set tolerance) greater than the expected drip rate), and/or whether the drops of fluid are flowing into the drip chamber 130 at a drip rate that is too low (e.g., the drops of fluid are flowing into the drip chamber 130 too slowly, such as when the recorded drip rate is at least 10% (or the set tolerance) lower than the expected drip rate). An absence of drops of fluid flowing into the drip chamber 130 may indicate the presence of a full upstream occlusion in the tube 115 and/or an empty reservoir 120. In some implementations, a low drip rate (e.g., when compared to a pump set drip rate) and/or a decreasing drip rate (e.g., when compared to previously recorded drip rates) may indicate that the drip chamber 130 and/or the reservoir 120 will become empty within a certain amount of time. Alternatively and/or additionally, a low drip rate and/or a decreasing drip rate may indicate that a partial upstream occlusion in the tube 115 is detected.

In some implementations, the pressure sensor 140B may detect and/or record one or more parameters, such as a fluid and/or air pressure in the reservoir 120 and/or the drip chamber 130. For example, based on the one or more parameters, the pressure sensor 140B may detect the presence of a vacuum in the tube 115 upstream from the pump 110 caused, for example, by a full upstream occlusion within the tube 115. Thus, an abnormal upstream flow condition in the pump may be detected when the pressure sensor 140B detects the presence of a vacuum in the tube 115 upstream from the pump 110.

Furthermore, the fluid level sensor 140C may be configured to determine a fluid level h in the drip chamber 130. The fluid level sensor 140C may determine the fluid level h in the drip chamber 130 at least by performing a series of time of flight measurements. In order to detect small fluctuations in the fluid level h, the fluid level sensor 140C may be configured to perform the time of flight measurements at a greater frequency than the frequency at which drops of fluid enter the drip chamber 130. For example, if the drip rate of the drops of fluid entering the drip chamber 130 is approximately 5 drops per minute (or 1 drop per 12 seconds), then the fluid level sensor 140C would perform time of flight measurements at a time of flight measurement rate that is greater than one time of flight measurement per 12 seconds. In other implementations, the time of flight measurements would be set (e.g., based on the expected drip rate) so that the fluid level sensor 140C performs each time of flight measurement between each drop of fluid into the drip chamber 130.

In some example embodiments, the fluid level sensor 140C may obviate the need for the drop sensor 140A and/or the pressure sensor 140B in the pump 110. For instance, by measuring small fluctuations in the fluid level h, the fluid level sensor 140C may also be capable of determining whether drops of the fluid are entering the drip chamber 130. The small fluctuations in the fluid level h may be indicative of drops of fluid entering the drip chamber 130. The small fluctuations may occur when the fluid level deviates from the initial or an expected fluid level by approximately 1% to 2%. In some implementations, the small fluctuations occur when the fluid level deviates by approximately 1% to 5%, 5% to 10%, 10% to 20% or greater from the initial or expected fluid level.

It should be appreciated that the fluid level sensor 140C may perform the time of flight measurements in any manner including, for example, by transmitting a signal (e.g., ultrasonic, light, and/or the like) through the fluid collected in the drip chamber 130 and measuring the quantity of time required for the signal to return to the fluid level sensor 140C. As used herein, time of flight may refer to the travel time of a signal (e.g., ultrasonic, light, and/or the like) through the fluid collected in the drip chamber 130. Accordingly, it should be appreciated that the time of flight measured by the fluid level sensor 140C may correlate to the fluid level present in the drip chamber 130.

Figure 2:
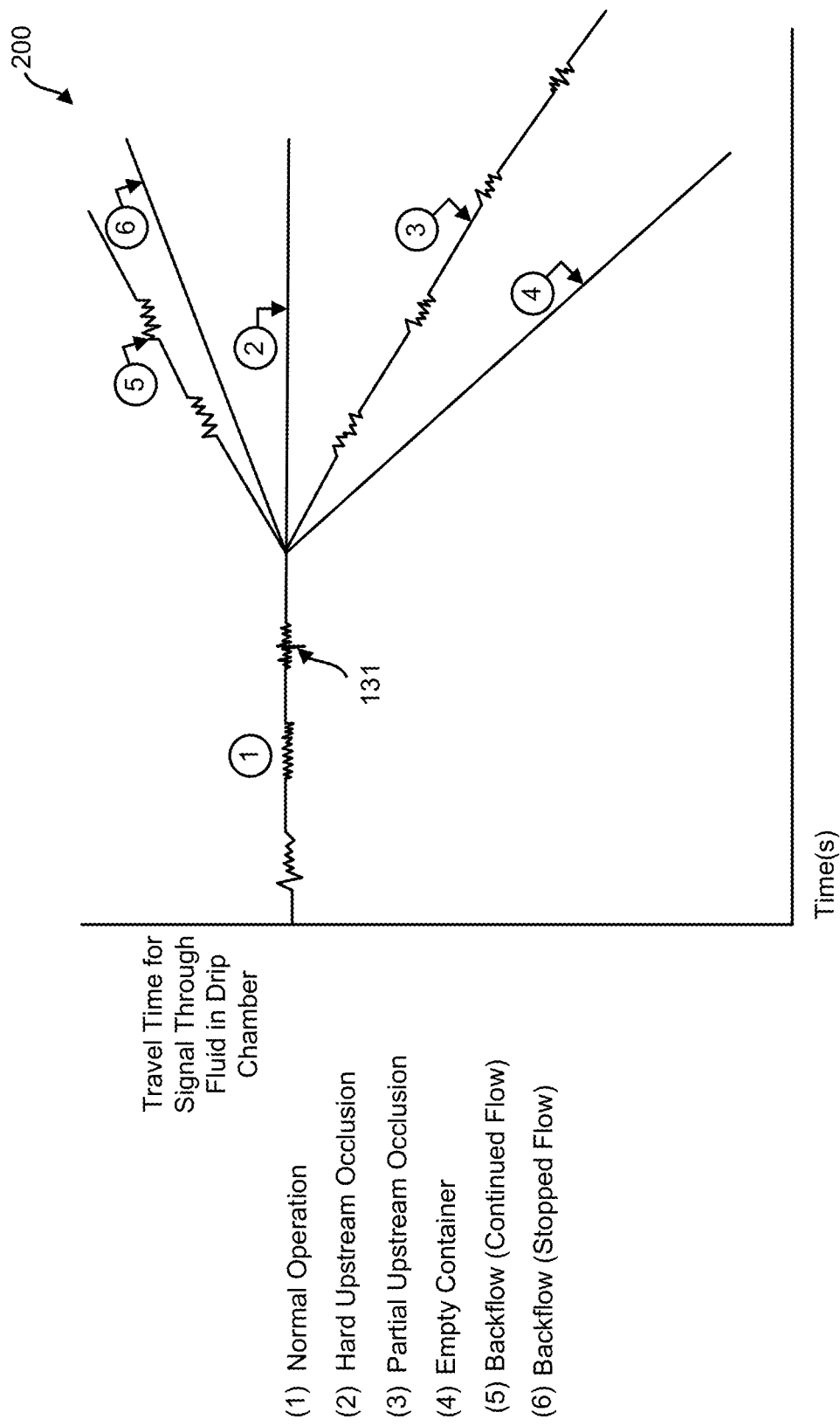
FIG. 2 depicts a graph illustrating the relationship between travel time for a signal through the fluid in a drip chamber and different upstream flow conditions in a pump, in accordance with some example embodiments.

In some example embodiments, the pump 110 may include a controller 105 configured to monitor the upstream flow characteristics of the pump 110 and detect one or more abnormal upstream flow conditions including, for example, a full upstream occlusion in the tube 115 (see FIG. 2 at (2)), a partial upstream occlusion in the tube 115 (see FIG. 2 at (3)), an empty reservoir 120 (see FIG. 2 at (4)), a backflow of fluid into the drip chamber 130 (see FIG. 2 at (5), (6)), and/or the like. For example, the controller 105 may detect a variety of abnormal upstream flow conditions based on outputs from the drop sensor 140A, the pressure sensor 140B, and/or the fluid level sensor 140C. The combination of outputs from the drop sensor 140A, the pressure sensor 140B, and/or the fluid level sensor 140C may enable the detection of abnormal upstream flow conditions that tend to evade conventional monitoring techniques. Some abnormal upstream flow conditions such as, for example, partial upstream occlusions in the tube 115 and/or backflows of fluid into the drip chamber 130, may be detected based on discrepancies in the outputs from the drop sensor 140A, the pressure sensor 140B, and/or the fluid level sensor 140C.

To further illustrate, FIG. 2 depicts a graph 200 illustrating the relationship between travel time for a signal through the fluid in the drip chamber 130 and different upstream flow conditions in the pump 110, in accordance with some example embodiments. Graph 200 shows the changes in the travel time of a signal through the fluid in the drip chamber 130 over time. As noted, the travel time of the signal through the fluid in the drip chamber 130 may correspond to the fluid level h inside the drip chamber 130. Though the illustrated changes in travel time of the signal through the fluid in the drip chamber 130 over time are representative of the various operating conditions (e.g., normal operation hard upstream occlusion, partial upstream occlusion, empty container, backflow (contained flow), and backflow (stopped flow)), other variations in the changes in travel time, such as spikes, valleys, etc. are also contemplated.

As shown in FIG. 2, the time of flight measured by the fluid level sensor 140C may remain relatively constant while the pump 110 is operating under normal conditions (1). That is, while the pump 110 is operating normally, the fluid level h inside the drip chamber 130 may undergo only small fluctuations as substantially equal quantities of fluid are flowing into and out of the drip chamber 130. As indicated in FIG. 2, fluctuations in fluid (e.g., caused by fluid dripping into the drip chamber 130, filling the drip chamber 130, and disrupting a surface of the fluid in the drip chamber 130) are shown as fluctuations 131.

By contrast, when a full upstream occlusion is present in the tube 115, the time of flight measured by the fluid level sensor 140C may remain fixed. Moreover, when a full upstream occlusion is present in the tube 115, the output from the pressure sensor 140B may indicate the presence of a vacuum inside the tube 115 caused by the full upstream occlusion. Meanwhile, the presence of the upstream occlusion may cause a stoppage in the flow of fluid into the drip chamber 130, although the lack of fluid flowing into the drip chamber 130 may also be attributable to the reservoir 120 being empty. Accordingly, in order to detect the full upstream occlusion in the tube 115, the controller 105 may rely on the outputs from the pressure sensor 140B and/or the fluid level sensor 140C. Alternatively and/or additionally, the controller 105 may supplement the outputs from the pressure sensor 140B and/or the fluid level sensor 140C with the output from the drop sensor 140A, when determining whether a full upstream occlusion is present in the tube 115.

Referring again to FIG. 2, the controller 105 may detect the presence of a partial upstream occlusion (3) in the tube 115 upstream from the pump 110 when the time of flight measurements from the fluid level sensor 140C indicate a decrease in the fluid level h inside the drip chamber 130 (as shown by a decrease in travel time at (3)), even though the output from the drop sensor 140A indicates that drops of fluid are flowing into the drip chamber 130.

As noted, the output from the drop sensor 140A may indicate the presence of a full upstream occlusion (e.g., at (2)) in the tube 115 and/or an empty reservoir 120. However, the controller 105 may be unable to determine, based on the output from the drop sensor 140A alone, whether the lack of drops of fluid flowing into the drip chamber 130 is caused by the full upstream occlusion in the tube 115 or the empty reservoir 120. In some example embodiments, the controller 105 may use the output from the fluid level sensor 140C to determine whether the lack of drops of fluid flowing into the drip chamber 130 is caused by the full upstream occlusion in the tube 115 or the empty reservoir 120. For example, as FIG. 2 shows, the controller 105 may determine that the reservoir 120 is empty (4) if, in addition to the lack of drops of fluid flowing into the drip chamber 130, the fluid level h inside the drip chamber 130 is decreasing at a threshold rate (e.g., by 10%, or 1% to 5%, 5% to 10%, 10% to 20% or greater) without exhibiting any small fluctuations caused by the addition of fluid flowing into the drip chamber 130 (as shown at 4).

In some example embodiments, the controller 105 may detect a backflow of fluids into the drip chamber 130 based on a rate of change in the fluid level h inside the drip chamber 130. Referring again to FIG. 2, the presence of a backflow may cause an accumulation of excess fluids inside the drip chamber 130 and may therefore trigger an increase (e.g., by 10%, or 1% to 5%, 5% to 10%, 10% to 20% or greater) in the travel time of a signal through the fluid in the drip chamber 130 (as shown at 5 and 6). Accordingly, the controller 105 may detect a backflow of fluids into the drip chamber 130 if the outputs from the fluid level sensor 140C indicates an increase in time of flight that corresponds to an increase in the fluid level h inside the drip chamber 130.

It should be appreciated that a backflow may occur with or without a flow of fluid from the tube 115 into the drip chamber 130. For example, in the event of a co-flow in which fluid is flowing from multiple reservoirs simultaneously, a backflow may occur while fluid continues to flow from the tube 115 into the drip chamber 130 (e.g., shown at (5)). An abnormal flow condition may occur during a co-flow scenario if a majority of the fluid entering into the drip chamber 130 is coming from one reservoir when the majority of the fluid should be coming from a different reservoir. Alternatively and/or additionally, a backflow may also occur while no fluid is flowing from the tube 115 into the drip chamber 130 (e.g., shown at (6)). When there are multiple reservoirs, a backflow with no fluid flowing into the drip chamber 130 may indicate the presence of another abnormal flow condition in which fluids are back flowing from one reservoir to another reservoir. Nevertheless, it should be appreciated that the controller 105 may detect a backflow in the tube 115 when the controller 105 encounters a significant increase in the time of flight measured by the fluid level sensor 140C, which indicates a significant increase in the fluid level h inside the drip chamber 130.

The sensors (e.g., the drop sensor 140A, the pressure sensor 140B, and the fluid level sensor 140C) may include one or more thresholds or tolerances to which the one or more measurements recorded by the sensors may be compared. The thresholds or tolerances may be predefined or otherwise preprogrammed on the pump 110. In other implementations, the thresholds or tolerances may be dynamic. For example, the thresholds or tolerances for the measurements recorded by the sensors may be adjusted by the pump 110 (e.g., by the controller 105) based on the type of fluid in the drip chamber 130, the size of the drip chamber 130 (e.g., a volume, width, height, depth, etc. of the drip chamber), and the like. In some implementations, the threshold and/or tolerance is an approximately 1% to 5%, 5% to 10%, 10% to 20% or greater deviation from an expected measurement (e.g., an expected drip rate, pressure, vacuum, fluid level, and the like) recorded by the sensors. Depending on the size of the drip chamber 130, the threshold and/or tolerance may also be adjusted by the pump system 110 (e.g., by the controller 105). For example, a drip chamber 130 having a large volume or other parameter may require a lower tolerance and/or threshold than a drip chamber 130 having a small volume or other parameter. In some implementations, the expected measurement may be preprogrammed into the pump system 100, and/or may be adjusted depending on one or more factors, such as a patient set, order, or prescription. In some examples, the reservoir 120, a prescription, or other patient order may be scanned by the pump system 100 to determine and set the expected measurement, the tolerance, and/or the threshold.

Figure 3:
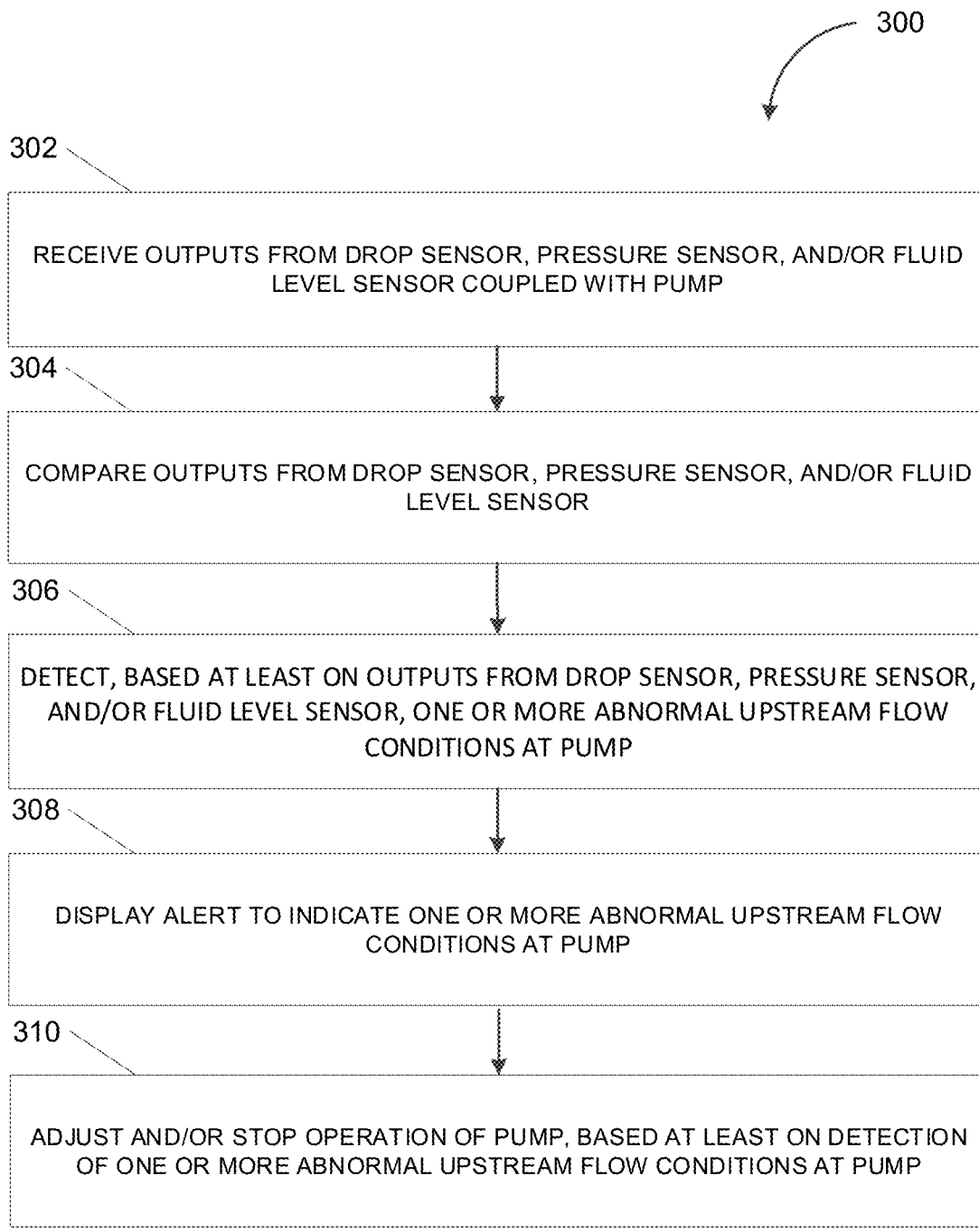
FIG. 3 depicts a flowchart illustrating a process for monitoring the upstream flow characteristics of a pump, in accordance with some example embodiments.

FIG. 3 depicts a flowchart illustrating a process 300 for monitoring the upstream flow characteristics of the pump 110, in accordance with some example embodiments. Referring to FIG. 3, the process 300 may be performed by the controller 105. As noted, the pump 110 may be coupled with the drop sensor 140A, the pressure sensor 140B, and/or the fluid level sensor 140C, which may provide outputs to the controller 105 that enables the controller 105 to detect a variety of abnormal upstream flow conditions. The controller 105 may receive the outputs from the drop sensor 140A, the pressure sensor 140B, and/or the fluid level sensor 140C via a bus, through a wired and/or a wireless connection.

At 302, the controller 105 may receive outputs from the drop sensor 140A, the pressure sensor 140B, and/or the fluid level sensor 140C coupled with the pump 110. For example, the controller 105 may receive, from the drop sensor 140A, outputs indicating whether drops of fluid are flowing into the drip chamber 130. Alternatively and/or additionally, the controller 105 may receive, from the pressure sensor 140B, outputs indicating whether a vacuum is present in the tube 115 upstream from the pump 110. Furthermore, the controller 105 may receive, from the fluid level sensor 140C, outputs indicating the fluid level h inside the drip chamber 130.

At 304, the controller 105 may compare the outputs of the drop sensor 140A, the pressure sensor 140B, and/or the fluid level sensor 140C with prior outputs of the drop sensor 140A, the pressure sensor 140B, and/or the fluid level sensor 140C, and/or with a predetermined threshold. The comparison enables a determination by the system of whether prior and/or recorded outputs are within a certain tolerance, are increasing, and/or are decreasing. For example, a low, high, increasing, and/or decreasing drip rate, pressure, and/or fluid level may indicate that one or more abnormal upstream flow conditions are occurring at the pump.

At 306, the controller 105 may detect, based at least on the outputs (and/or comparison of outputs) from the drop sensor 140A, the pressure sensor 140B, and/or the fluid level sensor 140C, one or more abnormal upstream flow conditions at the pump 110. In some example embodiments, the combination of outputs from the drop sensor 140A, the pressure sensor 140B, and/or the fluid level sensor 140C may enable the controller 105 to detect abnormal upstream flow conditions that tend to evade conventional monitoring techniques including, for example, a partial upstream occlusion in the tube 115 upstream from the pump 110, a backflow of fluids into the drip chamber 130, and/or the like. For instance, the controller 105 may detect the presence of the partial upstream occlusion in the tube 115 upstream from the pump 110 when the time of flight measurements from the fluid level sensor 140C indicate a decrease in the fluid level h in the drip chamber 130 even though the output from the drop sensor 140A indicates that drops of fluid are flowing into the drip chamber 130. Alternatively and/or additionally, the controller 105 may detect a backflow of fluids into the drip chamber 130 if the outputs from the fluid level sensor 140C indicates an increase in the fluid level h inside the drip chamber 130.

At 308, based on the detection of one or more abnormal upstream flow conditions at the pump 110, the pump system 100 (e.g., the controller 105) may indicate (e.g., via a display and/or user interface) to the patient, physician, or other user of the pump system 100 that one or more abnormal upstream flow conditions are occurring, and/or may occur. For example, the pump system 100 may, via a user interface of the pump system 100, display text, a flashing light, a noise, and/or another alert to indicate that one or more abnormal upstream flow conditions are occurring and/or may occur. The alert may indicate that the reservoir 120 needs to be refilled, and/or there is an issue with at least one component of the pump system 100 that needs to be fixed.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™.NET™, web services, or rich site summary (RSS). In some implementations, a UI may be included in a stand-alone client (for example, thick client, fat client) configured to communicate (e.g., send or receive data) in accordance with one or more of the aspects described. The communication may be to or from a medical device, diagnostic device, monitoring device, or server in communication therewith.

At 310, based on the detection of one or more abnormal upstream flow conditions at the pump 110, the pump system 100 (e.g., via the controller 105) may adjust one or more settings of the pump 110 (e.g., drip rate) and/or stop operation of the pump 110. For example, in some implementations, the pump 110 may automatically stop operation upon detection of one or more of the abnormal upstream flow conditions. In other implementations, operation of the pump 110 may be stopped and/or adjusted upon receipt of an input via a user interface of the pump system 100.

In some implementations, the controller 105 may be implemented as part of another flow control device such as a gravity controller or as a standalone device. When implemented as a standalone device, the controller 105 may communicate with a pump or other flow control device to exchange sensor readings, programming parameters, or detection results. For example, if a user programs a gravity controller with an expected flowrate, the flowrate may be used to perform the upstream flow characteristic assessment features described. In an implementation where the controller 105 is included in a device for monitoring the drip chamber, some of the upstream flow characteristic assessment features may be applied by sensing whether drops are falling and one or more characteristics of the liquid level within the drip chamber (e.g., increasing, constant, decreasing). In a standalone implementation, the controller 105 may include output elements to provide a perceivable output indicating the status of the infusion (e.g., nominal operation, started, finished, or detection of an upstream flow characteristic). A standalone controller may communicatively couple with a pump or other flow control device. In such implementations, the communication channel between the controller 105 and flow control device may be used to exchange information as described. The information may include sensed data, programming parameters, detection results, or control commands.

Figure 4:
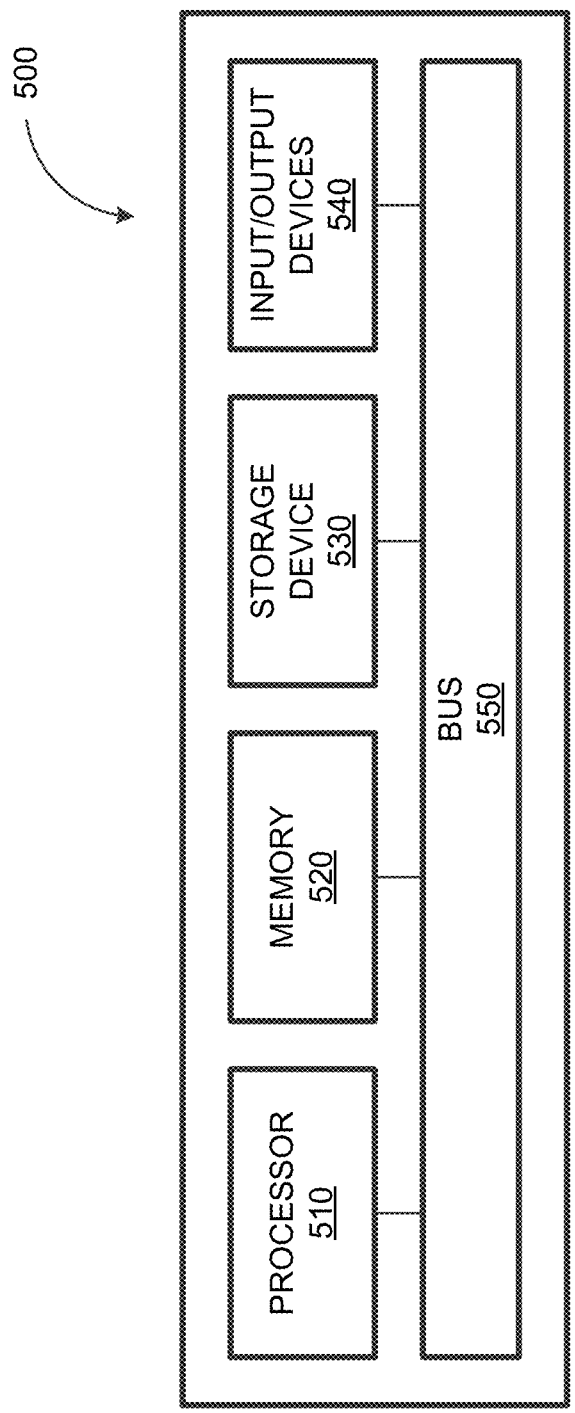
FIG. 4 depicts a block diagram illustrating a computing system, in accordance with some example embodiments.

FIG. 4 depicts a block diagram illustrating a computing system 500 consistent with implementations of the current subject matter. Referring to FIGS. 1-4, the computing system 500 may implement the controller 105 and/or any components therein.

As shown in FIG. 4, the computing system 500 can include a processor 510, a memory 520, a storage device 530, and input/output devices 540. The processor 510, the memory 520, the storage device 530, and the input/output devices 540 can be interconnected via a system bus 550. The processor 510 is capable of processing instructions for execution within the computing system 500. Such executed instructions can implement one or more components of, for example, the controller 105. In some implementations of the current subject matter, the processor 510 can be a single-threaded processor. Alternately, the processor 510 can be a multi-threaded processor. The processor 510 is capable of processing instructions stored in the memory 520 and/or on the storage device 530 to display graphical information for a user interface provided via the input/output device 540.

The memory 520 is a computer readable medium such as volatile or non-volatile that stores information within the computing system 500. The memory 520 can store data structures representing configuration object databases, for example. The storage device 530 is capable of providing persistent storage for the computing system 500. The storage device 530 can be a floppy disk device, a hard disk device, an optical disk device, a tape device, or other suitable persistent storage means. The input/output device 540 provides input/output operations for the computing system 500. In some implementations of the current subject matter, the input/output device 540 includes a keyboard and/or pointing device. In various implementations, the input/output device 540 includes a display unit for displaying graphical user interfaces.

According to some implementations of the current subject matter, the input/output device 540 can provide input/output operations for a network device. For example, the input/output device 540 can include Ethernet ports or other networking ports to communicate with one or more wired and/or wireless networks (e.g., a local area network (LAN), a wide area network (WAN), the Internet).

In some implementations of the current subject matter, the computing system 500 can be used to execute one or more computer software applications. Upon activation within the applications, the functionalities can be used to generate the user interface provided via the input/output device 540. For example, the user interface can be generated and presented to a user by the computing system 500 (e.g., on a computer screen monitor, etc.).

Figure 5A:
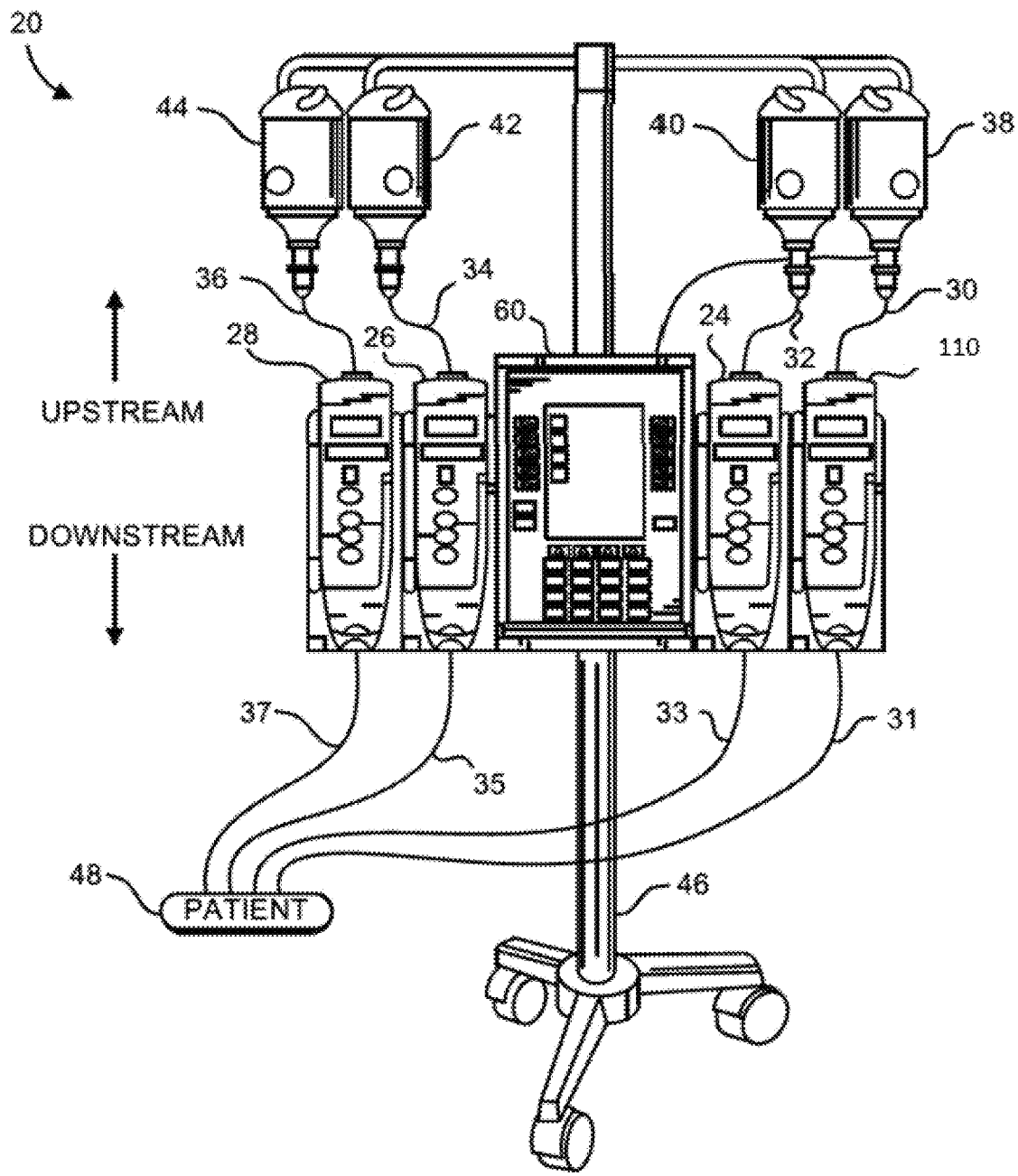
FIG. 5A depicts a front view of a patient care system, in accordance with some example embodiments.
Figure 5B:
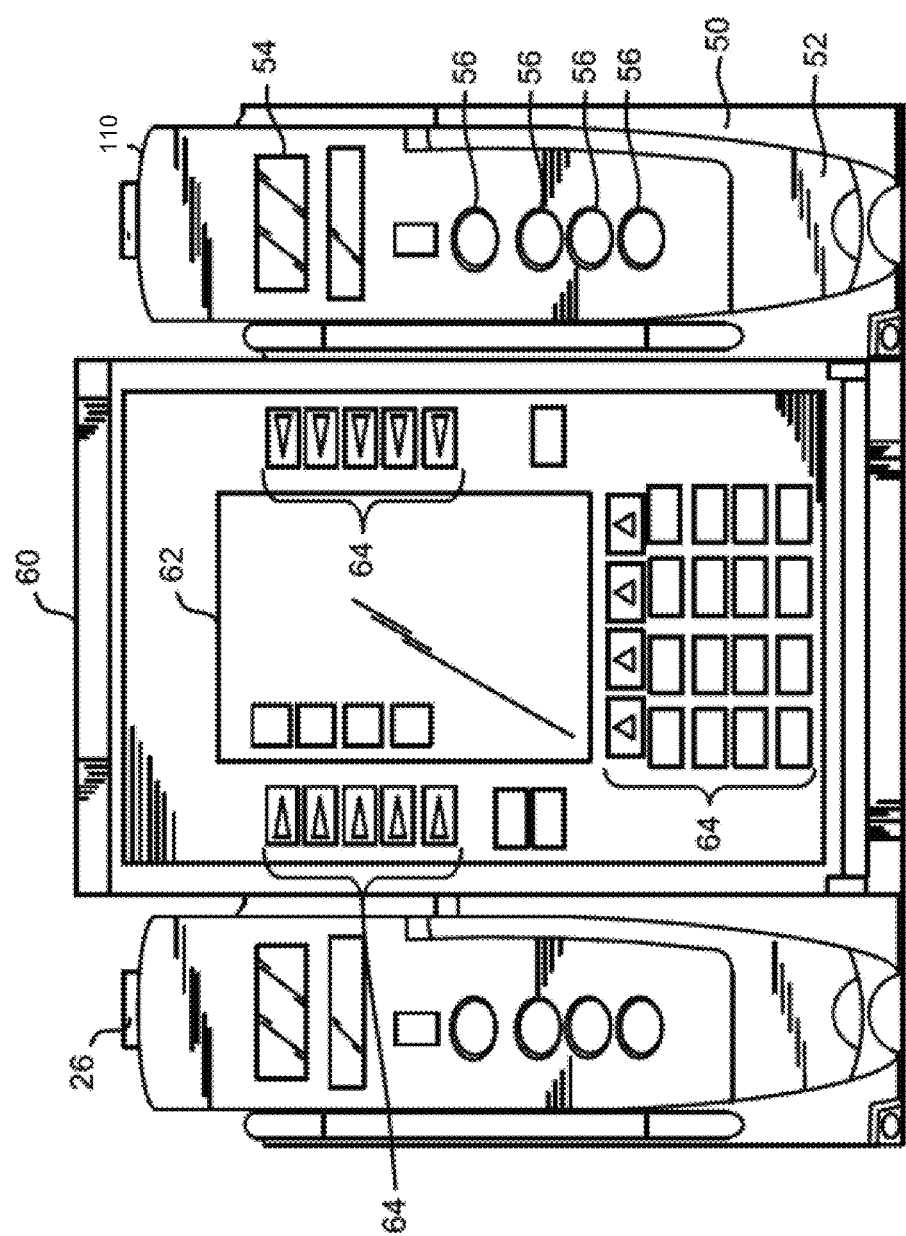
FIG. 5B depicts an enlarged view of a portion of a patient care system, in accordance with some example embodiments.
Figure 5C:
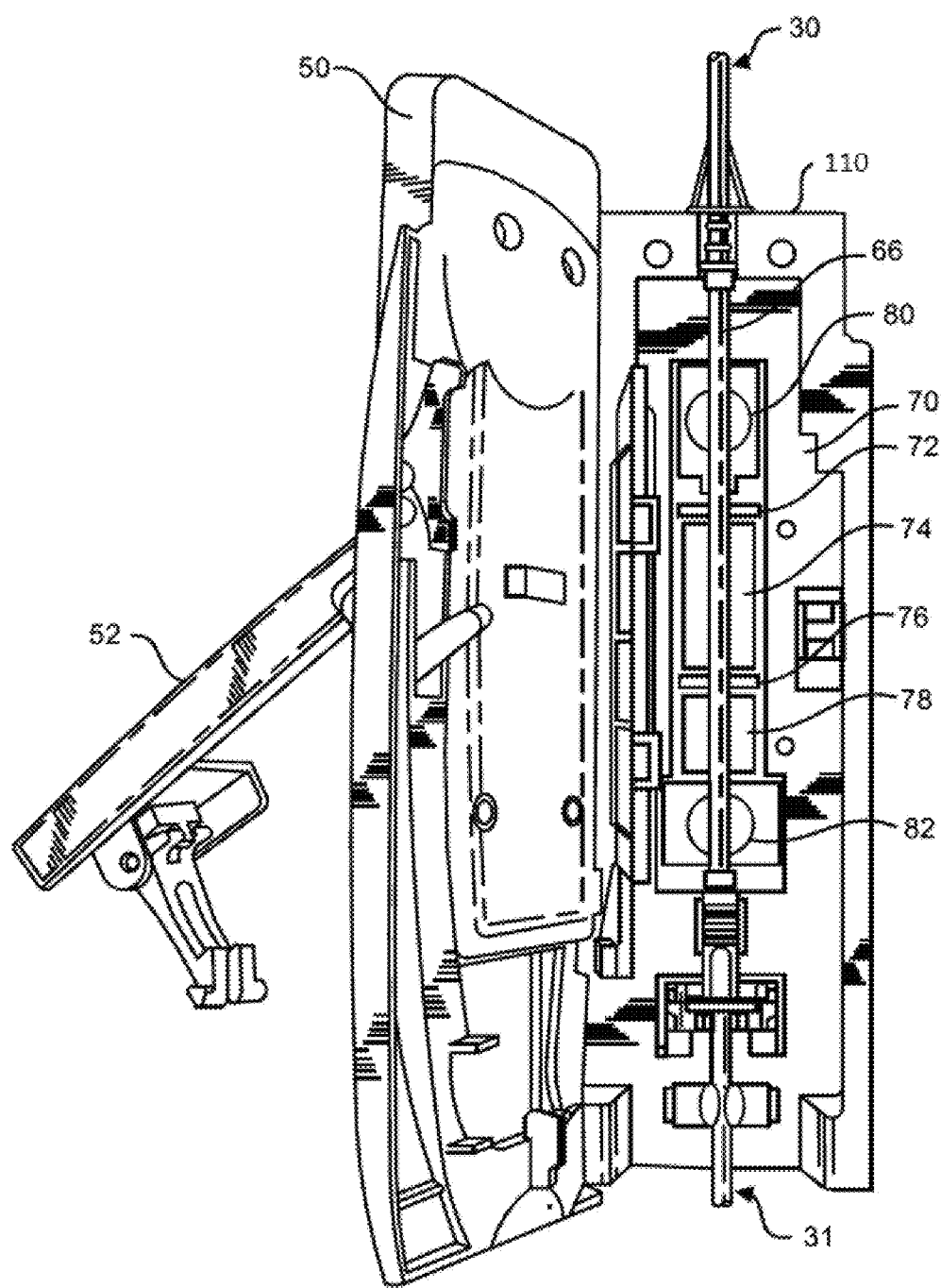
FIG. 5C depicts a perspective view of a pump, in accordance with some example embodiments.

In some example embodiments, the pump 110 may be part of a patient care system 20, which may include the pump system 100. FIGS. 5A-5C illustrate example embodiments of the patient care system 20, though other types of patient care systems may be implemented. Referring to FIG. 5A, the patient care system 20 may include the pump 110 as well as additional pumps 24, 26, and 28. Although a large volume pump (LVP) is illustrated, other types of pumps may be implemented, such as a peristaltic pump, a small volume pump (SVP), a syringe pump, an anesthesia delivery pump, and/or a patient-controlled analgesic (PCA) pump configured to deliver a medication (e.g., an anesthesia, and the like) to a patient. The pump 110 may be any infusion device configured to deliver a substance (e.g., fluid, nutrients, medication, and/or the like) to a patient's circulatory system or epidural space via, for example, intravenous infusion, subcutaneous infusion, arterial infusion, epidural infusion, and/or the like, or the pump 110 may be an infusion device configured to deliver a substance (e.g., fluid, nutrients, medication, and/or the like) to a patient's digestive system via a nasogastric tube (NG), a percutaneous endoscopic gastrostomy tube (PEG), nasojejunal tube (NJ), and/or the like.

As shown in FIG. 5A, each of the pump 110, 24, 26, and 28 may be fluidly connected with an upstream fluid line 30, 32, 34, and 36, respectively. Moreover, each of the four pumps 110, 24, 26, and 28 may also fluidly connected with a downstream fluid line 31, 33, 35, and 37, respectively. The fluid lines can be any type of fluid conduit, such as tubing, through which fluid can flow (e.g., the tubes 115, 150). At least a portion of one or more of the fluid lines may be constructed with a multi-layered configuration as described herein.

Fluid supplies 38, 40, 42, and 44 (e.g., the reservoir 120), which may take various forms but in this case are shown as bottles, are inverted and suspended above the pumps. Fluid supplies may also take the form of bags, syringes, or other types of containers. Both the patient care system 20 and the fluid supplies 38, 40, 42, and 44 may be mounted to a roller stand or intravenous (IV) pole 46.

A separate pump 110, 24, 26, and 28 may be used to infuse each of the fluids of the fluid supplies into the patient. The pumps 110, 24, 26, and 28 may be flow control devices that will act on the respective fluid line to move the fluid from the fluid supply through the fluid line to the patient 48. Because individual pumps are used, each can be individually set to the pumping or operating parameters required for infusing the particular medical fluid from the respective fluid supply into the patient at the particular rate prescribed for that fluid by the physician. Such medical fluids may comprise drugs or nutrients or other fluids.

Typically, medical fluid administration sets have more parts than are shown in FIG. 5A. Many have check valves, drip chambers, valved ports, connectors, and other devices well known to those skilled in the art. These other devices have not been included in the drawings so as to preserve clarity of illustration. In addition, it should be noted that the drawing of FIG. 5A is not to scale and that distances have been compressed for the purpose of clarity. In an actual setting, the distance between the bottles 38, 40, 42, and 44 and the pump modules 110, 24, 26, and 28 could be much greater.

Referring now to FIG. 5B, an enlarged view of the front of the patient care system 20 is shown. The pump 110 may include a front door 50 and a handle 52 that operates to lock the door in a closed position for operation and to unlock and open the door for access to the internal pumping and sensing mechanisms and to load administration sets for the pump. When the door is open, the tube can be connected with the pump, as will be shown in FIG. 5C. When the door is closed, the tube is brought into operating engagement with the pumping mechanism, the upstream and downstream pressure sensors, and the other equipment of the pump. A display 54, such as an LED display, is located in plain view on the door in this embodiment and may be used to visually communicate various information relevant to the pump, such as alert indications (e.g., alarm messages). The display 54 may otherwise be a part of or be coupled to the pump 110. Control keys 56 exist for programming and controlling operations of the pump as desired. The pump 110 also includes audio alarm equipment in the form of a speaker (not shown).

In the embodiment shown, a programming module 60 is attached to the left side of the pump 110. The programming module 60 may form and/or include the controller 105. In some embodiments, the programming module 60 forms a part of the pump 110. Other devices or modules, including another pump, may be attached to the right side of the pump 110, as shown in FIG. 5A. In such a system, each attached pump represents a pump channel of the overall patient care system 20. In one embodiment, the programming module is used to provide an interface between the pump 110 and external devices as well as to provide most of the operator interface for the pump 110.

The programming module 60 includes a display 62 for visually communicating various information, such as the operating parameters of the pump 110 and alert indications and alarm messages. The programming module 60 may additionally and/or alternatively display one or more of the measurements recorded by the drop sensor 140A, the pressure sensor 140B, and/or the fluid level sensor 140C described herein to the display 54. The programming module 60 may also include a speaker to provide audible alarms. The programming module or any other module also has various input devices in this embodiment, including control keys 64 and a bar code or other scanner or reader for scanning information from an electronic data tag relating to the infusion, the patient, the care giver, or other. The programming module also has a communications system (not shown) with which it may communicate with external equipment such as a medical facility server or other computer and with a portable processor, such as a handheld portable digital assistant ("PDA"), or a laptop-type of computer, or other information device that a care giver may have to transfer information as well as to download drug libraries to a programming module or pump.

The communications system may take the form of a radio frequency ("RF") (radio frequency) system, an optical system such as infrared, a Bluetooth system, or other wired or wireless system. The bar code scanner and communications system may alternatively be included integrally with the pump 110, such as in cases where a programming module is not used, or in addition to one with the programming module. Further, information input devices need not be hard-wired to medical instruments, information may be transferred through a wireless connection as well.

FIG. 5B includes a second pump 26 connected to the programming module 60. As shown in FIG. 5A, more pump modules may be connected. Additionally, other types of modules may be connected to the pump modules or to the programming module.

Turning now to FIG. 5C, the pump 110 is shown in perspective view with the front door 50 open, showing the upstream fluid line 30 and downstream fluid line 31 in operative engagement with the pump 110. The pump 110 directly acts on a tube 66 (also referred to as a pump segment) that connects the upstream fluid line 30 to the downstream fluid line 31 to form a continuous fluid conduit, extending from the respective fluid supply 38 (FIG. 5A) to the patient 48, through which fluid is acted upon by the pump to move fluid downstream to the patient. Specifically, a pumping mechanism 70 (also referred to herein as a "flow control device") acts as the flow control device of the pump to move fluid though the conduit. The upstream and downstream fluid lines and/or tube 66 may be coupled to a pump cassette or cartridge that is configured to be coupled to the pump 110, such as the type described in co-pending U.S. patent application Ser. No. 13/827,775, which is incorporated by reference herein.

The type of pumping mechanism may vary and may be for example, a multiple finger pumping mechanism. For example, the pumping mechanism may be of the "four finger" type and includes an upstream occluding finger 72, a primary pumping finger 74, a downstream occluding finger 76, and a secondary pumping finger 78. The "four finger" pumping mechanism and mechanisms used in other linear peristaltic pumps operate by sequentially pressing on a segment of the fluid conduit by means of the cam-following pumping fingers and valve fingers 72, 74, 76, and 78. The pressure is applied in sequential locations of the conduit, beginning at the upstream end of the pumping mechanism and working toward the downstream end. At least one finger is always pressing hard enough to occlude the conduit. As a practical matter, one finger does not retract from occluding the tubing until the next one in sequence has already occluded the tubing; thus at no time is there a direct fluid path from the fluid supply to the patient. The operation of peristaltic pumps including four finger pumps is well known to those skilled in the art and no further operational details are provided here.

In this particular embodiment, FIG. 5C further shows a downstream pressure sensor 82 included in the pump 110 at a downstream location with respect to the pumping mechanism. The downstream pressure sensor 82 is mounted to the flow control device 70 and is located adjacent and downstream in relation to the flow control device. The downstream pressure sensor is located downstream from the flow control device, that is, at a location between the patient 48 (FIG. 5A) and the flow control device, so that the connection of the correct fluid supply with the correct pump may be verified before any fluid is pumped to the patient.

With reference still to FIG. 5C, an upstream pressure sensor 80 (e.g., which may be and/or include the pressure sensor 140B) may also be included in the pump 110. The upstream pressure sensor is assigned to the flow control device or pumping mechanism 70 and, in this embodiment, is further provided as an integral part of the pump 110. It is mounted to the flow control device 70 and is located adjacent and upstream in relation to the flow control device. The upstream pressure sensor is located upstream from the flow control device, that is, at a location between the fluid supply 38 (FIG. 5A) and the flow control device, so that the connection of the correct fluid supply with the correct pump may be verified before any fluid is pumped to the patient. In an implementation where the source is a syringe, the flow control device 70 may be configured to press a plunger of the syringe to provide the infusion according to the programmed parameters. As noted above, the pump 10 may also include one or more other sensors, such as the drop sensor 140A, the pressure sensor 140B, and/or the fluid level sensor 140C.

One or more aspects or features of the subject matter described herein can be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices and associated interpretation software, and the like.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

In embodiments, data or other messages can be forwarded to a "remote" device or location," where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above. In addition, the logic flows depicted in the accompanying figures and/or described herein do not necessarily require the particular order shown, or sequential order, to achieve desirable results. For example, the logic flows may include different and/or additional operations than shown without departing from the scope of the present disclosure. One or more operations of the logic flows may be repeated and/or omitted without departing from the scope of the present disclosure. Other implementations may be within the scope of the following claims.

What is claimed is:

1. A system, comprising:
   at least one data processor; and
   at least one memory storing instructions, which when executed by the at least one data processor, result in operations comprising:
     receiving, from a fluid level sensor and at least one of a drop sensor and a pressure sensor, one or more outputs, the fluid level sensor and the at least one of the drop sensor and the pressure sensor coupled with a pump, the pump configured to move a fluid from a reservoir containing the fluid through a drip chamber, the fluid being moved through a tube upstream from the pump;
     detecting, based at least on the one or more outputs from the fluid level sensor and the at least one of the drop sensor and the pressure sensor, an abnormal upstream flow condition in the pump, the abnormal upstream flow condition including at least one of: a full upstream occlusion in the tube, a partial upstream occlusion in the tube, an empty reservoir, or a backflow of the fluid into the drip chamber; and
     adjusting, based on the detection of the abnormal upstream flow condition in the pump, operation of the pump.

2. The system of claim 1, wherein the fluid level sensor is configured to measure a fluid level in the drip chamber by at least transmitting a signal and measuring a quantity of time required for the signal to travel through the fluid in the drip chamber.

3. The system of claim 2, wherein the fluid level sensor is configured to detect drops of the fluid entering the drip chamber by at least measuring the fluid level in the drip chamber at a greater frequency than a frequency at which the drops of the fluid enter the drip chamber.

4. The system of claim 1, wherein the adjusting the operation of the pump comprises:
   generating a message to activate an element of the pump, wherein the element includes at least one of a valve, a light, or an audio alarm equipment; and
   transmitting the message to the pump.

5. The system of claim 1, wherein the full upstream occlusion in the tube is detected when a fluid level in the drip chamber remains fixed.

6. The system of claim 1, wherein the partial upstream occlusion in the tube is detected when a fluid level in the drip chamber decreases while drops of the fluid continue to enter the drip chamber.

7. The system of claim 6, wherein the partial upstream occlusion in the tube is detected when the drops of the fluid continue to enter the drip chamber at a drip rate that is less than an expected drip rate for the pump.

8. The system of claim 1, wherein the operations further comprise:
   predicting that the empty reservoir, the full upstream occlusion in the tube, and/or the partial upstream occlusion in the tube will occur when a fluid level in the drip chamber decreases while no drops of fluid enter the drip chamber.

9. The system of claim 1, wherein the backflow of the fluid into the drip chamber is detected based at least on an increase in a fluid level in the drip chamber.

10. The system of claim 1, wherein the operations further comprise:
    receiving, from the drop sensor and the pressure sensor, the one or more outputs, the drop sensor and the pressure sensor each coupled with the pump; and
    detecting, based at least on the one or more outputs of the drop sensor, the pressure sensor, and the fluid level sensor, the abnormal upstream flow condition in the pump.

11. The system of claim 1, further comprising:
    the pump;
    the reservoir containing the fluid;
    the drip chamber; and
    the fluid level sensor.

12. A method comprising:
    receiving, from a fluid level sensor and at least one of a drop sensor and a pressure sensor, one or more outputs, the fluid level sensor and the at least one of the drop sensor and the pressure sensor coupled with a pump, the pump configured to move a fluid from a reservoir containing the fluid through a drip chamber, the fluid being moved through a tube upstream from the pump;
    detecting, based at least on the one or more outputs from the fluid level sensor and the at least one of the drop sensor and the pressure sensor, an abnormal upstream flow condition in the pump, the abnormal upstream flow condition including at least one of: a full upstream occlusion in the tube, a partial upstream occlusion in the tube, an empty reservoir, or a backflow of the fluid into the drip chamber; and
    adjusting, based on the detection of the abnormal upstream flow condition in the pump, operation of the pump.

13. The method of claim 12, wherein the fluid level sensor is configured to measure a fluid level in the drip chamber by at least transmitting a signal and measuring a quantity of time required for the signal to travel through the fluid in the drip chamber.

14. The method of claim 13, wherein the fluid level sensor is configured to detect drops of the fluid entering the drip chamber by at least measuring the fluid level in the drip chamber at a greater frequency than a frequency at which the drops of the fluid enter the drip chamber.

15. The method of claim 12, wherein the adjusting the operation of the pump comprises causing activation of an element of the pump, wherein the element includes at least one of a valve, a light, or an audio alarm equipment.

16. The method of claim 12, wherein the full upstream occlusion in the tube is detected when a fluid level in the drip chamber remains fixed.

17. The method of claim 12, wherein the partial upstream occlusion in the tube is detected when a fluid level in the drip chamber decreases while drops of the fluid continue to enter the drip chamber.

18. The method of claim 17, wherein the partial upstream occlusion in the tube is detected when the drops of the fluid continue to enter the drip chamber at a drip rate that is less than an expected drip rate for the pump.

19. The method of claim 12, further comprising: predicting that the empty reservoir, the full upstream occlusion in the tube, and/or the partial upstream occlusion in the tube will occur when a fluid level in the drip chamber decreases while no drops of fluid enter the drip chamber.

20. The method of claim 12, wherein the backflow of the fluid into the drip chamber is detected based at least on an increase in a fluid level in the drip chamber.

\* \* \* \* \*